United States Patent [19]

Kinghorn et al.

[11] Patent Number: 4,808,409
[45] Date of Patent: Feb. 28, 1989

[54] LOW CARIOGENIC SWEETENING AGENTS

[75] Inventors: Alan D. Kinghorn; Cesar M. Compadre, both of Chicago; John M. Pezzuto, Glen Ellyn, all of Ill.

[73] Assignee: Board of Trustees, University of Illinois, Urbana, Ill.

[21] Appl. No.: 641,526

[22] Filed: Aug. 16, 1984

[51] Int. Cl.$^4$ .................. A61K 7/16; C07C 49/713
[52] U.S. Cl. .................................. 424/439; 424/49; 426/548; 574/690; 568/377
[58] Field of Search .................. 568/377; 426/538; 424/548, 49, 58, 439; 514/690

[56] References Cited

U.S. PATENT DOCUMENTS

| | | | |
|---|---|---|---|
| 3,839,421 | 10/1974 | Schwieber | 568/377 |
| 4,136,119 | 1/1979 | Hunter et al. | 568/377 |
| 4,245,109 | 1/1981 | Mayer et al. | 568/377 |
| 4,246,292 | 1/1981 | Konst et al. | 568/377 |

FOREIGN PATENT DOCUMENTS 58-183639 10/1983 Japan .................................. 568/377

OTHER PUBLICATIONS

Compadre et al., *Science*, vol. 227, pp. 417–419, (1/25/85).
Bohlmann et al., *Phytochemistry*, vol. 17, pp. 475–482 (1978).
Takeda et al., *Chemical Abstracts*, vol. 76, No. 59779h, (1972).
Bohlmann et al., *Chemical Abstracts*, vol 90, No. 104133v, (1979).
Harwood et al., *Chemical Abstracts*, vol. 94, No. 103585q, (1981).

*Primary Examiner*—Bruce D. Gray
*Assistant Examiner*—Grace Hanks
*Attorney, Agent, or Firm*—Philip Hill

[57] ABSTRACT

Racemic hernandulcin, a sesquiterpene, possesses a sweetness intensity about three orders of magnitude greater than that of sucrose. It is non-mutagenic and non-toxic under conventional assay procedures. In addition to attractive utility in foods, beverages and pharmaceutical compositions, it affords a low-cariogenic, essentially non-nutritive sweetening agent for inclusion in oral hygiene products.

10 Claims, 1 Drawing Sheet

STRUCTURE OF HERNANDULCIN

STRUCTURE OF HERNANDULCIN

ANALOGS OF HERNANDULCIN

| $R_1$ | $R_2$ | $R_3$ | n |
|---|---|---|---|
| $-CH_2CH_3$ | $-H$ | $-CH_2CH=C{<}^{CH_3}_{CH_3}$ | 2-8 |
| $-(CH_2)_2CH_3$ | $-CH_2CH_3$ | | |
| $-(CH_2)_3CH_3$ | $-(CH_2)_2CH_3$ | $-CH_2CH_2CH{<}^{CH_3}_{CH_3}$ | |
| | $-(CH_2)_3CH_3$ | $-CH_2CH=CH-CH_3$ | |
| $-CH_2OH$ | | $-CH_3$ | |
| $-CH_2COOH$ | | $-CH_2CH_3$ | |
| | | $-CH{<}^{CH_2OH}_{CH_3}$ | |
| | | $-CH{<}^{CH_2COOH}_{CH_3}$ | |

LOW CARIOGENIC SWEETENING AGENTS

This invention was made with Government support under contract NO1-DE-02425, awarded by the National Institute of Dental Research, National Institutes of Health. The Government has certain rights in this invention.

BACKGROUND OF THE INVENTION

It is generally agreed that there continues to be a need for highly effective non-nutritive and non-cariogenic sweetening agents. Insufficient information exists for a rational design of novel, sweet-tasting molecules which can serve as prototypes for the development of sweeter and safer compounds.

Incidental to a study of perfumes and odor-modifying agents, Kovats, et al., in U.S. Pat. No. 3,928,456, discovered that certain cycloaliphatic, unsaturated ketones possessed flavoring and taste-modifying properties. Similar discoveries were reported by Schulte-Elte, et al., in U.S. Pat. No. 4,147,672.

Resort to the plant kingdom has afforded several types of intensely sweet compounds, including a dihydroisocoumarin (phyllodulcin), certain glycosides, and the proteinaceous thaumatin, all of which serve as sugar substitutes in one or more countries.

An optically active, sweet sesquiterpene, hernandulcin, has been isolated from the herb *Lippia dulcis* Trev. (Verbenaceae) which is indigenous to Mexico. Following elucidation of its structure, methods have been devised for the synthesis of related structures.

SUMMARY OF THE INVENTION

This invention relates to novel, low-cariogenic sweetening agents, including racemic (±)-hernandulcin, their method of manufacture and their use in a variety of beverages, foodstuffs, and pharmaceutical compositions, including oral hygiene compositions. These agents are many times greater than sucrose while being essentially non-nutritive.

Racemic hernandulcin has been found to be non-mutagenic and non-toxic and thus especially suited for use in a broad variety of food products, including candies and other confectioner's products. The sweetening agent compositions of this invention are based on a sesquiterpene structure, having adjacent asymmetric centers involving one carbon atom of the cycloaliphatic ring and its adjacent substituent carbon atom, serving as the anchoring member of the aliphatic sidechain.

The novel beverage, food, and pharmaceutical compositions of this invention employ small but taste-effective concentrations of the sweetening agents.

The process of manufacture for these novel sweetening agents affords an optimized, yet simple, procedure for isolation of the desired products.

DESCRIPTION OF THE INVENTION

This invention relates to certain novel and low cariogenic sweetening agents, useful as a non-nutritive dietary substitute or supplement for sucrose, as a food or beverage additive, and as a flavor component of various pharmaceutical compositions, including oral hygiene products. The sweetening agents of this invention are characterized as possessing two adjacent asymmetric centers involving both a cycloaliphatic ring structure and an alkyl substituent. A typical sweetening agent of this invention is hernandulcin, whose structure is set forth in FIG. 1. The optically active dextro stereoisomer of hernandulcin has been found to occur in the Mexican herb, *Lippia dulcis* Trev., known as a sweet plant by the Aztec people. The inventors have elucidated the structure of hernandulcin, devised a method for synthesis of hernandulcin and analogs thereof, and determined their utility for inclusion in foodstuffs and related products for human or animal use.

Hernandulcin, or 6-(1',5'-dimethyl-1'-hydroxyhex-4'-en-1'-yl)-3-methyl-2-cyclohexen-1-one, in its optically active form, is extremely sweet, being some 1,000 times as sweet as sucrose when compared on a molar basis (at 0.27 molar sucrose) and about 1,500 times as sweet when compared on a weight basis. The synthetic, racemic mixture of levo and dextro stereoisomers of hernandulcin likewise possesses a very attractive sweetness intensity, about one-half that of the isolated natural product.

Figure 2:
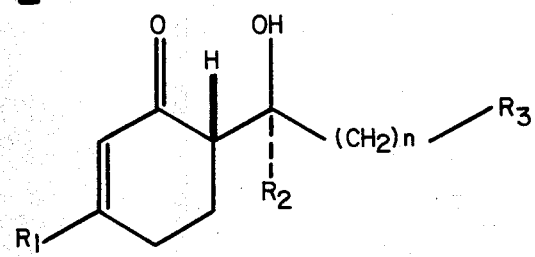
FIG. 2 presents selected analogs of hernandulcin, including analogs having enhanced solubility in water.

The sweetness of hernandulcin is believed to be associated with asymmetry of the 6 and 1' carbon atoms as well as with the proximity of the keto and hydroxyl groups. Various analogs of hernandulcin are set forth in FIG. 2, where taste properties related to the oxygen-containing groups remain essentially unaffected by substitution of hydrogen or a lower alkyl group at the $R_2$ position. Variation in substituents $R_1$ and $R_3$ can be effected to include alkyl or alkene groups and particularly hydroxyl or carboxyl groups for increasing the water solubility of the sweetening agent. Hernandulcin is soluble in water to the extent of about 0.5 gram per liter. While this is generally sufficient, because of the intense sweetness exhibited, modification of structure to improve water solubility in various foodstuff formulations is available as may be desired. For example, hydroxyl-containing substituents at $R_1$ or $R_3$ positions may be further modified by conversion to disodium phosphate esters or monosodium succinate esters. Similarly, carboxyl-containing substituents at $R_1$ or $R_3$ positions may be further modified by conversion to alkyl esters, such as methyl esters, to alkali metal salts, such as a sodium or potassium salt, or to glycosyl esters, such as a glucose or rhamnose ester.

Hernandulcin is non-mutagenic when tested with *Salmonella typhimurium* strain TM677 and is non-toxic for mice as assessed by acute toxicity studies employing oral administration. Hernandulcin is relatively stable to hydrolysis over a wide pH range in tests conducted at temperatures up to about 60° C. Its principal decomposition products are 3-methyl-2-cyclohexen-1-one and 6-methyl-5-hepten-2-one. These products, particularly the latter, were essentially non-toxic for mice when tested as above.

These characteristics of the synthetic, racemic (±)-hernandulcin make possible its use in a variety of beverages as a sweetening agent. Where a greater water solubility is desired a selected analog, as discussed above, may be employed. Any particular beverage formulation, containing a taste-effective concentration of the sweetening agent of this invention, may also contain other additive agents as desired for taste modification or intensity. In general, the sweetening agents of this invention should be employed at concentrations in the range from about 0.05 to about 0.50 grams per liter of aqueous solution. In liquid concentrates an analog having greater solubility is preferred. In solid powders, a preferred analog is an alkali metal salt derivative inasmuch as hernandulcin and many of the specified analogs are oils. An alternative formulation employs the sweetening agent adsorbed on other solid components of the powdered concentrate for beverage use. In any intended beverage formulation, any one or more of the sweetening agents of this invention may be employed.

When employed as a sweetening agent or flavor modifier in various foodstuffs, including candies and other confectioner's products, any one or combination of the agents of this invention, preferably racemic hernandulcin, may be incorporated as an additive in the desired product. The sweetening agent may be an ingredient of a recipe for sauces, dressings, or condiments. The agent may also be incorporated in canned fruits, vegetables, and the like, or in normally frozen or refrigerated products such as meats, pastries, packaged meals or entrees, or dairy products such as ice cream.

When employed in a foodstuff composition the concentration of the sweetening agent of this invention should be at a taste-effective level, considering the interplay of all of the other ingredients. Generally, a concentration level within the range from about 0.005 to about 0.5 wt. % will be effective, with a preferred range being from about 0.01 to about 0.1 wt. %.

The sweetening agents of this invention are particularly useful in a variety of pharmaceutical compositions as a replacement for agents such as sucrose which are often employed in high concentrations. Such pharmaceutical compositions may be provided in liquid form, as thickened products, including gels, or as solid formulations, in each instance conforming generally to the concentration ranges set forth above for both liquid and solid formulations.

The low cariogenicity of the sweetening agents of this invention is strongly suggestive of use in various oral hygiene compositions. When employed as an ingredient in such products very low concentrations can be taste-effective. A particularly preferred employment of the agents of this invention involves liquid oral hygiene compositions such as mouthwashes. Another effective use of these agents is in thickened gels or pastes employed as dentifrices. Use in solid oral hygiene compositions is equally effective.

Following a determination of the structure of hernandulcin, a method for synthesis of the racemic mixture of stereoisomers was devised and reaction conditions were optimized to permit improvement of product yield to the range of about 50 mol. % of the theoretical value.

The synthetic reaction involves the condensation of cyclic and acyclic moieties to provide what is believed to be the first known sesquiterpene intense sweetening agent. Although the synthesis of hernandulcin is described here, the disclosed technique can be employed for synthesis of the analogs of FIG. 2 with only minor modifications.

More specifically, racemic hernandulcin is preferably prepared by condensing 3-methyl-2-cyclohexen-1-one with 6-methyl-5-hepten-2-one in solution in a cyclic ether solvent, such as tetrahydrofuran or dioxane, in the presence of a lithium- or boron-containing condensation agent, such as a lithium amide or a boron triflate. Suitable amides include lithium diisopropylamide, lithium cyclohexylisopropyl-amide, lithium hexamethyl- disilylamide, and lithium 2,2,6,6-tetra-methylpiperidide. A typical boron triflate is di-n-butylboron trifluoromethyl sulfonate. Preferably the reaction solution also contains a small amount of 2,2'-dipyridyl. The reaction is conducted, with mixing, at a temperature within the range from about $-78°$ to $-0°$ C., preferably about $-20°$ C. to about $-10°$ C., and most preferably about $-15°$ C., and under an inert atmosphere, usually afforded by gaseous nitrogen. Agitation is continued for from about 5 to about 15 minutes and the reaction mixture is quenched with the addition of a saline solution, such as 10% aqueous ammonium chloride. The reaction product is extracted from the aqueous mixture with, for example, diethyl ether, recovered by distillation of the ether solvent, and the recovered product oil is distributed on high-surface area silica gel. Elution of the product, employing, for example, a hexane-acetone elution solvent, preferably comprising about 97 vol. % hexane and about 3 vol. % acetone, occurs with the hernandulcin product being recovered from selected adjacent fractions in very high purity.

The following procedures and results are exemplary, without limitation, of the products and process of this invention.

EXAMPLE I

Dried and chopped L. dulcis herb (900 g.) was extracted with petroleum ether (b.p. range 60°–80°, 4×4 liters). Extracts were combined and evaporated to produce 7.35 g. of a sweet-tasting residue. A portion (1.4 g.) of this residue was chromatographed over silica gel (particle size 0.063–0.2 mm., 120 g.) contained in a glass column (25 cm.×1.5 cm.). Separation was achieved by gradient elution with mixtures of hexane and acetone, ranging in polarity from 100% hexane to 90% hexane-10% acetone. Fractions (10 ml. each) were monitored by thin-layer chromatography on silica gel, using hexane-acetone (9:1) as developing solvent and 60% sulfuric acid as visualizing reagent. The sweet constituent of L. dulcis was found to be present in fractions 47–59 that were eluted with 90% hexane-10% acetone. These fractions were combined, and the sweet compound was purified by preparative thin-layer chromatography on silica gel plates developed with the solvent system hexane-acetone (17:3). Further quantities of sweet isolate were generated by repetition of the chromatographic steps outlined above on additional quantities of plant material.

EXAMPLE II

The sweet isolate obtained in Example I, which was named hernandulcin, was a colorless oil, $[\alpha]_D^{25} + 109°$ (c. 0.11, ethanol), and exhibited the molecular formula $C_{15}H_{24}O_2$, based on a high-resolution electron impact mass spectral measurement of the molecular ion appearing at 236.18005 amu. Infrared and ultraviolet absorption maxima typical of an alpha-beta unsaturated ketone functionality and an intramolecularly-bonded hydroxy group were observed. The $^1$H-NMR (nuclear magnetic resonance) spectrum revealed the presence in hernandulcin of a tertiary methyl group on a carbon bearing the hydroxy group, and three methyl groups attached to double bonds and two olefinic protons. Based on these spectral features, hernandulcin was assigned as a monocyclic sesquiterpene of the bisabolane type. The $^{13}$C-NMR spectrum showed discrete signals for all fifteen carbons when fully proton-decoupled, and was comparable with analogous data reported for other sesquiterpenes in this series. The spectra are summarized in Table I.

Additional evidence for the structure of this compound was obtained by the identification of two principal degradation products, 6-methyl-5-hepten-2-one and 3-methyl-2-cyclohexen-1-one, that were produced when hernandulcin was treated with strong bases or heated to 140° C. These products were identical spectrally to authentic samples obtained from commercial sources. This degradation pattern is consistent with the tendency of other beta-ketols to experience reverse-aldol condensation when treated similarly.

Figure 1:
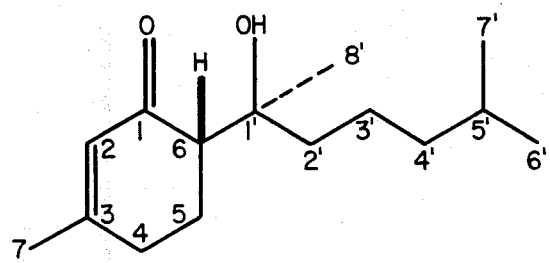
FIG. 1 presents the structure of hernandulcin, as established by spectroscopic and degradation procedures.

The relative configuration of hernandulcin as indicated in FIG. 1 was inferred not only by the existence of strong hydrogen bonding between the hydroxy and carbonyl groups, but also because of the demonstrated absence in its $^1$H-NMR spectrum of any nuclear Overhauser enhancement. The latter would be expected by the interaction of the C-14 methyl protons and the C-6 proton if, in fact, these functionalities were arranged in a syn conformation. Thus, the number of possible structures for natural hernandulcin was reduced to two, namely, either (6R,'R)- or (6S,1'S)-6-(1',5'-dimethyl-1'-hydroxyhex-4'-en-1-yl)-3-methyl-2-cyclohexen-1-one.

EXAMPLE III

Optimized reaction conditions were employed in the synthesis of racemic hernandulcin. To a cold ($-15°$ C.) solution of lithium diisopropylamide (0.92 g.; 8.5 mmol.) and a few mg. of 2,2'-dipyridyl in 15 ml. anhydrous tetrahydrofuran, 0.93 g. (8.5 mmol.) of 3-methyl-2-cyclohexen-1-one were added. The reaction mixture was maintained under an atmosphere of nitrogen, and then 1.07 g. (8.5 mmol.) of 6-methyl-5-hepten-2-one were incorporated. After stirring for 5 min., the reaction was quenched with 10% aqueous ammonium chloride, and the product extracted into diethyl ether (3×20 ml.). The combined diethyl ether fractions were washed with 15 ml. of a saturated solution of sodium chloride, and were dried over anhydrous sodium sulfate. On removal of solvent, 1.9 g. of a yellow liquid were obtained. Purification over silica gel (0.05-0.2 mm; 250 g.) by elution with hexane-acetone (97:3) produced pure racemic-hernandulcin (970 mg.; 4.1 mmol.). The synthetic racemic hernandulcin was sweet, and was indistinguishable from natural hernandulcin in its spectroscopic (UV, IR, NMR, MS) and chromatographic (TLC) characteristics.

EXAMPLE IV

Stability studies on synthetic hernandulcin were carried out, in both buffer solutions and when neat. The first of these manipulations was conducted by storage of this compound in citrate-phosphate-borate buffer solutions, at the pH levels 2, 3, 4, 6, 7, 8, 10, and 12. Hernandulcin was stored in each solution at a concentration of about 0.1 wt. %, at both room temperature and 60° C., for two weeks. Solutions were exposed to the atmosphere after their constitution.

Compound decomposition was assessed by counting the number of zones apparent by TLC analysis 1 hour, 3 hours, 6 hours, 24 hours, 1 week and 2 weeks after solution composition. Hernandulcin exhibited a single purple zone on silica gel plates when developed in the solvent system hexane-acetone (17:3), and visualized with 60% sulfuric acid by heating at 110° for 5 minutes. At room temperature, which was used to indicate the stability of hernandulcin under normal handling, no compound breakdown was evident for any of the pH levels used after up to two weeks of storage. Similarly, no decomposition was observed for any solution when stored for up to 24 hours at 60° C., a temperature chosen to represent that which might be experienced during food processing. However, after 1 week and 2 weeks at 60° C., substantial breakdown was apparent in all solutions, with greater degrees of decomposition being observed at the acid and alkaline pH extremes, although hernandulcin was detectable at all pH's at these time intervals. No attempt was made to quantify the degree of breakdown of hernandulcin.

An assessment of the thermostability of hernandulcin was conducted by storing a sample at 100° C. for 24 hours, and comparing it by TLC with the unheated compound. After such treatment, approximately 60% of the compound remained unchanged, and about a 10% conversion to each of 3-methyl-2-cyclohexen-1-one and 6-methyl-5-hepten-2-one was observed. These figures represent approximations obtained by calculating TLC zone areas.

EXAMPLE V

The actue toxicity of synthetic hernandulcin, 3-methyl-2-cyclohexene-1-one, and 6-methyl-5-hepten-2-one was determined in male Swiss-Webster mice. Compounds were suspended in a minimum volume of 1% sodium carboxymethylcellulose, and were administered by oral intubation at the doses indicated in Table II. Mortality was determined up to 14 days after compound administration, and it may be seen from Table II that only 3-methyl-2-cyclohexene-1-one exhibited an $LD_{50}$ of less than 2 g/kg, as expressed after 24 hours. Hernandulcin and 6-methyl-5-hepten-2-one produced no mortality at doses up to 2 g/kg body weight.

In Table III, body weight variations are shown over a two-week period for synthetic hernandulcin and 6-methyl-5-hepten-2-one. For hernandulcin there were no significant variations from control values for the body weights in mice dosed at 1.0 g/kg and 2.0 g/kg. In corresponding studies performed on 6-methyl-5-hepten-2-one, however, the Day 14 total body weight values were significantly different from control values.

EXAMPLE VI

The mutagenic potential of synthetic hernandulcin was examined by a forward mutation assay utilizing *Salmonella typhimurium* strain TM677, according to known procedures. No significant mutagenic activity was noted when hernandulcin was assayed either in the presence or absence of a metabolic activating system derived from the livers of Aroclor 1254-pretreated rats.

EXAMPLE VII

Magnitude estimation studies of sweetness intensity and sweetness pleasantness on natural hernandulcin were performed by a human taste panel, made up of 17 volunteers who had passed a screening test administered earlier, and who were thus considered reliable subjects. Seven concentrations of sucrose (0.031, 0.062, 0.125, 0.25, 0.5, 1.0 and 2.0M) and of natural hernandulcin ($1.06 \times 10^{-5}$, $2.11 \times 10^{-5}$, $4.24 \times 10^{-5}$, $8.47 \times 10^{-5}$, $1.69 \times 10^{-4}$, $3.39 \times 10^{-4}$ and $6.78 \times 10^{-4}$M) were prepared in distilled water. Solutions were presented to the subjects in a randomized fashion and were sampled in duplicate. After tasting, each solution was expectorated, and the mouth was washed with distilled water. Results of the comparison are presented in Table IV.

Using an open-ended magnitude ratio scale, sucrose was rated for its sweetness intensity only, while hernandulcin was rated for sweetness, after-taste, off-taste intensities and pleasantnesses, as well as bitterness intensity.

The results, shown in Table V, indicate that the concentration of the hernandulcin solution approximately equal to a standard 0.27M sucrose solution in sweetness intensity was $2.5 \times 10^{-4}$M. Thus on a molar basis, hernandulcin was perceived by the panel to be about 1,000 times sweeter than a 0.27M sucrose solution, or about 1,500 times sweeter on a weight basis. However, hernandulcin was judged by the panel to be less pleasant than sucrose, and to exhibit significant off- and aftertastes, as well as a moderate bitterness.

EXAMPLE VIII

Cariogenicity tests were conducted with synthetic, racemic hernandulcin. In a first test, the ability of microbes to utilize this sweetener source as a nutrient and convert it to acidic by-products was determined. *S. mutans* utilized this sweetener as a carbohydrate source and produced $2.6 \times 10^{-5}$ mEq acid/min. when the concentration of the sweetener was 5,000 micrograms per unit volume. This was a relatively low rate of acid production, as compared to sucrose. Acid production from sucrose (500 micrograms per unit volume) was $2.8 \times 10^{-4}$ mEq acid/min. under identical conditions. On a weight basis the rate of acid production was one hundred-fold less than that attained from sucrose.

In a second test, the ability of the test compound to inhibit acid production from sucrose by *S. mutans* was determined. The test compound failed to reduce the rate of acid production from *S. mutans*, even when the test compound was used in a 10-fold concentration over sucrose (428 micrograms per unit volume sucrose and 5,000 micrograms per unit volume sweetener).

TABLE I $^1$H— and $^{13}$C—NMR Spectral Data for Hernandulcin, recorded using Deuteriochloroform as Solvent with Tetramethylsilane as Internal Standard. Abbreviations: s, singlet; d, doublet; t, triplet; q, quartet; m, multiplet; br, broad; $\underline{J}$, coupling constants in hertz; $\delta$, chemical shift; M, multiplicity. Chemical shifts were assigned by selective double-irradiation experiments.

| Carbon | $^1$H—NMR* $\delta$,M,$\underline{J}$(Hz) | $^{13}$C—NMR $\delta$,M |
|---|---|---|
| C-1 | | 204.0,s |
| C-2 | 5.88,s(br) | 127.4,d |
| C-3 | | 163.6,s |
| C-4 | 2.34,m | 31.2,t |
| C-5 | 1.69,m;2.05,m | 25.0,t |
| C-6 | 2.42,dd,14.1,4.5 | 52.0,d |
| C-7 | 1.97,s(br) | 24.1,q |
| C-1' | | 73.9,s |
| C-2' | 1.48,t(br),8.0 | 40.1,t |
| C-3' | 2.05,m;2.15,m | 21.5,t |
| C-4' | 5.19,t(br),8.1 | 124.4,d |
| C-5' | | 131.4,s |
| C-6' | 1.68,s(br) | 25.7,q |
| C-7' | 1.63,s(br) | 17.6,q |
| C-8' | 1.18,s | 23.6,q |
| OH | 5.29,s | |

*Recorded at 360 MHz.
Recorded at 90.8 MHz.

TABLE II

Acute Toxicity Testing of Hernandulcin, and the Hernandulcin Decomposition Products 3-Methyl-2-cyclohexen-1-one and 6-Methyl-5-hepten-2-one, Following Oral Administration of Mice[a]

| Compound | Dose Administered (g/kg) | | Estimated LD$_{50}$ (g/kg) |
|---|---|---|---|
| | 1.0 | 2.0 | |
| Hernandulcin[b,c] | 0/10[d] | 0/10[d] | >2.0 |
| 3-Methyl-2-cyclo-[b] hexen-1-one | — | 8/10[e,f] | 1.6 ± 0.13 |
| 6-Methyl-5-hepten-[b] 2-one | 0/9[d] | 0/9[d] | >2.0 |

[a]Male Swiss-Webster mice (9 or 10 animals per dose).
[b]Purity > 99%.
[c]Synthetic compound used [mixture of two enantiomers, i.e., (R,R)— and (S,S-)—forms].
[d]Mortality = number of mice dying within 14 days/number of starting mice.
[e]Mortality = number of mice dying within 24 hours/number of starting mice.
[f]Other mortality figures were: 0/10, 2/10, 4/10, 5/10 and 10/10 at, respectively, 1.1, 1.3, 1.4, 1.6, and 2.4 g/kg.

TABLE III

Variation in Body Weight in Mice Following Oral Administration of Hernandulcin and the Hernandulcin Decomposition product, 6-Methyl-5-hepten-2-one

| Compound | Dose (g/kg) | Body Weight (g) of Test Animals at Time Intervals[a,b] | | | | |
|---|---|---|---|---|---|---|
| | | Pre-Drug | Day 1 | Day 3 | Day 7 | Day 14 |
| Hernandulcin[c,d] | 1.0[e] | 29.3 ± 0.8 | 27.1 ± 0.8 | 26.7 ± 0.8 | 27.9 ± 0.8 | 28.1 ± 0.8 |
| Controls | —[e] | 29.3 ± 0.8 | 27.1 ± 0.8 | 26.8 ± 0.8 | 27.4 ± 0.8 | 28.8 ± 0.8 |
| Hernandulcin[c,d] | 2.0[e] | 26.0 ± 0.9 | 25.6 ± 0.9 | 26.3 ± 0.9 | 26.0 ± 0.9 | 27.6 ± 0.9 |
| Controls | —[e] | 27.8 ± 0.9 | 27.4 ± 0.9 | 27.5 ± 0.9 | 27.0 ± 0.9 | 29.1 ± 0.9 |
| 6-Methyl-5-hepten-2-one[c] | 1.0[f] | 27.7 ± 0.8 | 28.2 ± 0.8 | 26.3 ± 0.8 | 24.7 ± 0.9 | 28.0 ± 0.8 |
| 6-Methyl-5-hepten-2-one[c] | 2.0[f] | 28.8 ± 0.8 | 28.6 ± 0.8 | 26.8 ± 0.9 | 25.0 ± 0.9 | 24.5 ± 0.8[g] |
| Controls | —[f] | 28.9 ± 0.8 | 29.6 ± 0.8 | 29.3 ± 0.8 | 26.2 ± 0.8 | 29.2 ± 0.8 |

[a]No significant differences (p < 0.05) were found in treated animals compared with control animals on one-way analysis of variance, except where indicated.
[b]Male Swiss-Webster mice.
[c]Purity > 99%.
[d]Synthetic compound.
[e]Number of animals in each group = 10.
[f]Number of animals in each group = 9.
[g]Significant difference from controls on one-way analysis of variance.

TABLE IV

Comparison of Sweetness Intensity and Sweetness Pleasantness of Sucrose and Hernandulcin, as determined by a human taste panel using an open-ended magnitude ratio scale*.

| Concentration Tasted | | Sweetness Intensity | | Sweetness Pleasantness | |
|---|---|---|---|---|---|
| Sucrose (M) | Hernandulcin ($M \times 10^{-5}$) | Sucrose[#] | Hernandulcin | Sucrose[#] | Hernandulcin |
| 0.031 | 1.06 | 6.6 (2.44) | 9.7 (4.19) | −3.2 (6.44) | 1.2 (5.58) |
| 0.062 | 2.11 | 7.8 (1.96) | 8.8 (2.37) | −1.6 (7.61) | 2.6 (6.00) |
| 0.125 | 4.24 | 21.9 (3.30) | 8.8 (3.18) | 19.2 (5.23) | 1.2 (4.18) |
| 0.25 | 8.47 | 38.1 (4.43) | 15.8 (4.10) | 31.8 (6.34) | 4.9 (7.67) |
| 0.50 | 16.9 | 44.4 (4.63) | 39.7 (3.52) | 37.8 (5.96) | 24.8 (7.99) |
| 1.0 | 33.9 | 75.5 (4.73) | 44.4 (5.45) | 2.5 (9.57) | 8.2 (10.70) |
| 2.0 | 67.8 | 89.1 (2.93) | 62.7 (5.59) | −20.2 (12.69) | −16.2 (9.78) |

*The test panel was composed of seventeen previously trained volunteers.
Intensity attributes (means and standard errors) were in the range of 0–100.
Hedonic attributes (pleasantness-unpleasantness) carry a + or − sign. The data (means and standard errors) were normalized to span the range −100 (extremely unpleasant) to +100 (extremely pleasant). A hedonic value of 0 is therefore neutral, neither pleasant nor unpleasant.
[#]A solution of 0.27 m was determined graphically as providing a standard panel response to sucrose intensity.

TABLE V

Sensory Test Values for the *Lippia dulcis* Sweet Constituent, Hernandulcin, at a Concentration Which Matches the Sweetness of 0.27 M Sucrose [a,b]

| Sweetner | Concentration (M) | Sweetness | | Off-Taste | | After-taste | | Bitterness |
|---|---|---|---|---|---|---|---|---|
| | | Intensity | Pleasantness | Intensity | Pleasantness | Intensity | Pleasantness | |
| Sucrose | 0.27 | 40 | | | | | | |
| Hernandulcin[c,d] | $2.5 \times 10^{-4}$ | 40 | 15 | 33 | −5 | 30 | 0 | 15 |

[a]Data obtained by human taste panel using an open-ended magnitude scale.
[b]Data obtained by 17 participants.
[c]Two replicates at each concentration were tested.
[d]Naturally occurring substance.

We claim:

1. Racemic 6-(1',5'-dimethyl-1-hydroxyhex-4'-en-1'-yl)-3-methyl-2-cyclohexen-1-one.

2. Beverage compositions comprising a taste-effective concentration of the low-cariogenic, water-soluble sweetening agent racemic 6-(1',5'-dimethyl-1'-hydroxyhex-4'-en-1'-yl)-3-methyl-2-cyclohexen-1-one.

3. The beverage compositions of claim 2 wherein the concentration of sweetening agent is within the range from about 0.05 to about 0.50 grams per liter of aqueous solution.

4. Food compositions comprising a taste-effective concentration of the low-cariogenic, water-soluble sweetening agent, racemic 6-(1',5'-dimethyl-1'-hydroxyhex-4'-en-1'-yl)-3-methyl-2-cyclohexen-1-one.

5. The food compositions of claim 4 wherein the concentration of sweetening agent is within the range from about 0.005 to about 0.5 wt. %.

6. Pharmaceutical compositions comprising a taste-effective concentration of the low-cariogenic, water-soluble sweetening agent, racemic 6-(1',5'-dimethyl-1'-hydroxyhex-4'-en-1'-yl)-3-methyl-2-cyclohexen-1-one.

7. Liquid pharmaceutical compositions of claim 6 wherein the concentration of sweetening agent is within the range from about 0.05 to about 0.50 grams per liter of aqueous. solution.

8. Thickened oral hygiene compositions of claim 6 wherein the concentration of sweetening agent is within the range from about 0.005 to about 0.5 wt. %.

9. Solid pharmaceutical compositions of claim 6 wherein the concentration of sweetening agent is within the range from about 0.005 to about 0.5 wt. %.

10. Pharmaceutical compositions of claim 6 comprising oral hygiene compositions.

* * * * *